United States Patent [19]

Watson

[11] 4,182,658
[45] Jan. 8, 1980

[54] EMERGENCY POLYMERIZATION INHIBITOR SYSTEM FOR VINYL AROMATIC COMPOUNDS

[75] Inventor: James M. Watson, Big Spring, Tex.

[73] Assignee: Cosden Technology, Inc., Big Spring, Tex.

[21] Appl. No.: 854,379

[22] Filed: Nov. 23, 1977

[51] Int. Cl.² ............................................. B01D 3/34
[52] U.S. Cl. ................... 203/9; 203/DIG. 7; 203/69; 585/5; 585/952; 585/956
[58] Field of Search ................. 203/9, DIG. 7, 67, 69; 260/666.5, 669 A

[56] References Cited

U.S. PATENT DOCUMENTS

| | | | |
|---|---|---|---|
| 2,240,764 | 5/1941 | Dreisbach et al. | 203/9 |
| 3,366,702 | 1/1968 | Moriarty | 203/9 |
| 3,988,212 | 10/1976 | Watson | 203/9 |
| 4,033,829 | 7/1977 | Higgins et al. | 203/9 |

Primary Examiner—Hiram H. Bernstein
Attorney, Agent, or Firm—Schwartz, Jeffery, Schwaab, Mack, Blumenthal & Koch

[57] ABSTRACT

Disclosed is a method for preventing the polymerization of a readily polymerizable vinyl aromatic compound during distillation at elevated temperatures within a distillation apparatus which is subject to an emergency condition, such as a power outage. This method comprises force feeding a supplemental polymerization inhibitor having a high solubility in the vinyl aromatic compound, and a long duration of efficiency, into each of the distillation vessels of a conventional distillation apparatus in an amount sufficient to prevent polymerization therein. In the preferred embodiment the supplemental polymerization inhibitor comprises 2,6-dinitro-p-cresol and meta-nitro-para-cresol.

11 Claims, 1 Drawing Figure

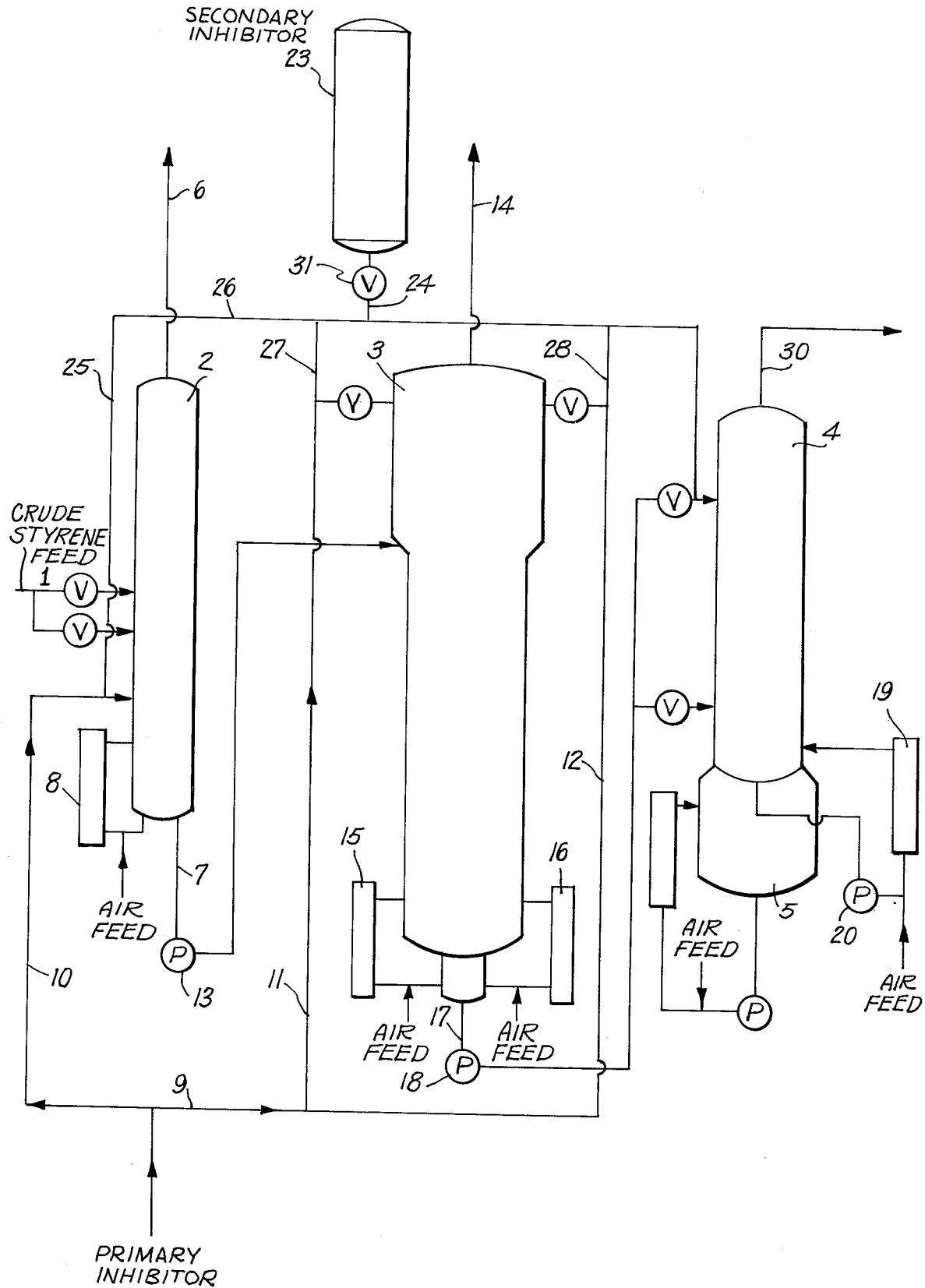

EMERGENCY POLYMERIZATION INHIBITOR SYSTEM FOR VINYL AROMATIC COMPOUNDS

BACKGROUND OF THE INVENTION

The present invention relates to a process for preventing the polymerization of readily polymerizable vinyl aromatic compounds during distillation with chemical polymerization inhibitors. More particularly, the present invention relates to a method for inhibiting the polymerization of styrene, substituted styrene, divinyl benzene, and polyvinyl benzenes, during distillation at elevated temperatures under emergency conditions in which the normal polymerization inhibitor system is rendered inoperative.

It is well known that vinyl aromatic compounds such as monomeric styrene, lower alkylated styrene, e.g., alpha-methyl styrene, and the like polymerize readily at elevated temperatures. Accordingly, it is common practice to adopt measures to prevent the polymerization of these compounds during distillation. Typically, these measures comprise pumping a chemical polymerization inhibitor into the distillation columns of a conventional distillation train. To this end, many chemical polymerization inhibitors have been developed which are highly efficacious in prevent the polymerization of vinyl aromatic compounds during distillation under normal situations. There may be mentioned, for example, N-nitrosophenylhydroxyl amine, para-nitroso-N, N-dimethylaniline, N-nitroso diphenyl amine U.S. Pat. No. 3,816,265) a phenothiazine-tertiary butyl catechol (TBC) chemical inhibitor system, N-nitrosomethylaniline, sulfur, TBC, mixtures of sulfur and TBC, dinitro-o-cresol, dinitrophenol, and meta-nitro-parap cresol.

Occasionally, however, an emergency situation develops, such as a power outage, which renders a given distillation facility unexpectedly inoperative. In these instances long periods may ensue during which a vinyl aromatic feed is trapped within the distillation train at elevated temperatures with the absence of any substantial heat transfer from the liquids contained in the distillation column bottoms, and with the inhibitor pumping system rendered inoperative. In the event of a power failure, therefore, a considerable amount of time may lapse during which a vinyl aromatic compound feed is at elevated temperatures with polymerization inhibition provided only by the small quantity of inhibitor present with the vinyl aromatic compound in the distillation train. Such limited quantities of conventional inhibitors, hereinafter referred to as primary inhibitors, are inadequate however to provide sufficient long-term polymerization inhibition to the vinyl aromatic compound feed. The low solubility in the vinyl aromatic compound, the requirement for air activation, and/or the short half-life reduces the efficacy of many of the most effective distillation polymerization inhibitors during prolonged power outage situations. Ocassionally, in fact, the protection provided by the limited quantities of primary inhibitor present within a distillation train subject to such conditions has been so grossly inadequate as to result in complete polymerization within the distillation apparatus. Such a situation represents not only a significant potential danger to the personnel and property at the distillation facility, but the costs in labor and downtime can be very significant where extensive polymerization of the vinyl aromatic compound trapped within the distillation train occurs. Normally, solid polymer can be removed from a polymerization vessel only by a tedious manual operation.

While several polymerization inhibitors are known, such as dinitro-o-cresol and dinitrophenol, which do not suffer from the aforementioned deficiencies, and therefore could be expected to provide reliable prolonged control of polymerization, the acute toxicity which these compounds exhibit militates against their selection as either emergency or primary inhibitors. Of course, the present invention may be utilized with such inhibitors if desired, and such use would still be within the spirit and scope of the invention. Moreover, while many compounds are known to provide prolonged polymerization inhibition under room temperature conditions, such as storage, under distillation at elevated temperatures, these compounds are ineffectual in inhibiting polymerization. It is apparent therefore that the prior art has failed to develop a satisfactory polymerization inhibitor which provides adequate protection at elevated temperatures under emergency conditions. Accordingly, in view of the recent emphasis upon developing safety measures for chemical installations, and particularly in view of several regional power failures which have occurred within the last several years, it would be desirable to provide a method whereby the polymerization of a vinyl aromatic compound within a distillation apparatus at elevated temperatures may be prevented during emergency conditions in which the normal primary inhibitor is ineffective.

SUMMARY OF THE INVENTION

Accordingly, it is an object of the present invention to provide a method for inhibiting the polymerization of a vinyl aromatic compound within a distillation apparatus at elevated temperatures subject to emergency situations in which the primary polymerization inhibitor is ineffective.

It is another object of the present invention to provide a method for preventing the polymerization of a vinyl aromatic compound within a distillation apparatus at elevated temperatures under conditions in which the primary inhibitor addition system is rendered inoperative.

Yet another object of the instant invention is to provide a method for inhibiting the polymerization of a vinyl aromatic compound within a distillation apparatus subject to a complete power failure.

Still another object of the instant invention is to provide a supplemental inhibitor addition system for inhibiting the polymerization of vinyl aromatic compounds within a distillation apparatus at elevated temperatures for use under emergency situations.

It is an additional object of the present invention to provide an emergency polymerization inhibitor addition system which is independent of electrical energy requirements.

It is a specific object of the present invention to provide an emergency polymerization inhibitor system for use with a styrene distillation apparatus.

In accomplishing the foregoing and other objects, there has been provided in accordance with the present invention a method for preventing the polymerization of a readily polymerizable vinyl aromatic compound during distillation at elevated temperatures within a distillation apparatus having at least one distillation column and having a primary polymerization inhibitor addition system which is subject to an emergency condition which renders the addition system inoperative.

This method comprises pre-preparing a pressurized solution of a readily soluble polymerization inhibitor in an aromatic hydrocarbon diluent for use as a supplemental emergency polymerization inhibitor, and in the event of an emergency which immobilizes the primary polymerization inhibitor addition system, force feeding this solution into each of the distillation vessels of the distillation apparatus in an amount sufficient to prevent polymerization of vinyl aromatic compound therein.

Broadly, the present invention is advantageous for preventing the polymerization of any vinyl aromatic compound within a distillation apparatus at elevated temperatures. Additionally, any compound which is readily soluble and exhibits a high efficacy for inhibiting the polymerization of vinyl aromatic compounds at elevated temperatures may comprise the supplemental inhibitor of the instant invention. However, in a preferred embodiment, the present invention provides a particularly advantageous emergency method for inhibiting the polymerization of styrene within a distillation system at elevated temperatures using 2,6-dinitro-p-cresol or meta-nitro-para-cresol as a supplemental polymerization inhibitor. In this aspect of the method according to the present invention, a large capacity pressurized vessel is utilized to inject an effective quantity of the 2,6-dinitro-p-cresol or meta-nitro-para-cresol inhibitor in an aromatic hydrocarbon diluent into each of the distillation columns of a conventional styrene distillation train upon the onset of an emergency condition.

The amount of the supplemental inhibitor necessary to inhibit the polymerization of the vinyl aromatic compounds will vary over a broad range depending upon various factors such as the temperature of the distillation apparatus and the length of the emergency situation. Typically, however, it has been found that the injection of a minimum of 1000 ppm of the 2,6-dinitro-p-cresol or meta-nitro-para-cresol retarder relative to the vinyl aromatic compound in each distillation vessel provides reliable prolonged control of polymerization in the event of a power outage.

Through the provision of a supplemental emergency inhibitor system, the present invention thus greatly reduces the amount of polymer formed within a distillation apparatus subject to a power outage. The present invention thus provides a contingency system whereby the quality of a vinyl aromatic compound trapped within a distillation system subject to an emergency situation is preserved until provision can be made to either remove the vinyl aromatic compound trapped within the distillation apparatus or to institute procedures to rectify the emergency condition. Moreover, by preventing the polymerization of the vinyl aromatic compound trapped within a distillation apparatus, the present invention accrues the additional advantages of preventing the formation of deleterious polymer deposits within the distillation columns.

Yet other objects and advantages of the present invention will become apparent to the skilled artisan upon examination of the following detailed description of the present invention, taken in conjunction with the figure of drawing, wherein:

BRIEF DESCRIPTION OF THE DRAWING

The single drawing shows a schematic diagram of a typical three-column distillation train comprising a first fractionation column, a recycle column, and a finish column, employing the supplemental emergency inhibitor system of the present invention.

DETAILED DESCRIPTION OF THE PREFERRED EMBODIMENTS

The present invention provides a method for preventing the polymerization of vinyl aromatic compounds under conditions in which the usual polymerization inhibitor system is either inoperative, or is inadequate to provide the requisite inhibitor protection. To this end, applicant has found that by providing a supplemental emergency inhibitor system which is independent of energy considerations, the aforementioned problem can be overcome. By utilizing such a supplemental system, applicant is able to provide sufficient quantities of polymerization inhibitor to achieve effective polymerization control during prolonged emergency situations. The present invention thus contemplates that any suitable means which is independent of external energy considerations may be employed for feeding the supplemental inhibitor into the distillation apparatus upon the occurrence of a debilitating emergency such as a power outage. Advantageously, however, it is preferred in the instant invention that the supplemental inhibitor addition means comprises a large capacity pressurized vessel for force feeding an effective quantity of a supplemental polymerization inhibitor solution into the immobilized distillation apparatus. The pressurized vessel may be of any suitable construction well known to those in the art, the only limitation being that it is of sufficient size to deliver an effective amount of the inhibitor solution into the distillation apparatus. Suitably, the pressurized vessel is of the bottom dish feedpoint type, as this type of vessel provides the most effective delivery of the inhibitor solution.

As has been emphasized, the pressurized vessel is employed to force feed an effective quantity of a supplemntal polymerization inhibitor solution into each of the distillation columns of a distillation apparatus subject to an emergency condition. This solution comprises a suitable polymerizable inhibitor in an aromatic hydrocarbon diluent. The aromatic hydrocarbon diluent may comprise any suitable volatile aromatic hydrocarbon which is compatible with the vinyl aromatic feed and which permits optimum distribution of the supplemental polymerization inhibitor within each of the distillation columns of the distillation apparatus. By way of example, this diluent may include benzene, toluene, ethylbenzene, or styrene. Preferably, however the volatile aromatic diluent comprises ethylbenzene since use of this diluent permits the distribution of the supplemental polymerization inhibitor to be optimized within the recycle column of a conventional distillation train. Applicant has found that this section of a typical distillation train is most subject to the formation of thermal polymer. Moreover, applicant has found that the amount of the thermal polymer formed within a distillation apparatus can be significantly reduced by optimizing the distribution of the polymerization inhibitor within this column. Accordingly, the use of ethylbenzene as an aromatic hydrocarbon diluent is most preferred, since it facilitates optimum polymerization inhibitor distribution.

Successful operation of the method of the present invention requires that an effective quantity of the polymerization inhibitor solution be kept available in the event of a contingency. It is essential, therefore, in order that an effective quantity of the supplemental inhibitor be available for injection into the distillation apparatus, that the solubility of the particular supplemental inhibitor chosen at room temperature in the aromatic hydrocarbon diluent be such that it remains in solution even upon periods of prolonged storage. Moreover, a high solubility at room temperature is necessary to protect against plugging of the pressurized vessel outlet upon prolonged disuse of the emergency inhibitor system in order to insure an instant supply of the supplemental inhibitor in the event of a contingency. Accordingly, any polymerization inhibitor which has a high solubility at room temperature in the aromatic hydrocarbon diluent, and preferably in ethylbenzene, may be employed as the emergency inhibitor contemplated by the instant invention.

In the preferred embodiment, however, 2-6-dinitro-p-cresol or meta-nitro-para-cresol is utilized as the supplemental inhibitor. The use of these inhibitors accrues significant advantages which make them ideal choices for use in the instant invention. Most importantly, 2,6-dinitro-p-cresol and meta-nitro-para-cresol each have a solubility of greater than 25 weight % in ethylbenzene at room temperature. This high solubility not only assures that an effective quantity of the supplemental inhibitor will remain in solution upon prolonged storage at room temperature, but also allows the preparation of a highly concentrated supplemental inhibitor solution, thereby permitting a pressurized vessel with a smaller working capacity to be utilized without sacrificing the amount of supplemental inhibitor which can be delivered into the distillation apparatus. Moreover, the high efficacy and the long duration of effectiveness of these inhibitors enable them to provide reliable prolonged control of polymerization. These properties thus render both 2,6-dinitro-p-cresol and meta-nitro-para-cresol ideal candidates for use as a supplemental polymerization inhibitor when compared with other known prior art inhibitors. By way of comparison, the solubility of sulfur in styrene or ethylbenzene at room temperature is too low to allow injection of the amounts needed for effective protection. Similarly, the relatively short half-life of n-nitroso-diphenylamine dictates against use of this inhibitor for prolonged emergency protection. Furthermore, the relatively low toxicity of 2,6-dinitro-p-cresol and meta-nitro-para-cresol favors the use of these materials as emergency inhibitors when compared with the highly toxic dinitro-o-cresol or dinitrophenol.

As has been aforementioned, applicant has found that the injection of at least 1000 ppm of the 2,6-dinitro-p-cresol or meta-nitro-para-cresol inhibitor into each distillation column of a conventional distillation train, relative to the amount of vinyl aromatic compound contained therein, provides effective prolonged polymerization control. Accordingly, in the practice of the present invention, the emergency inhibitor addition system must be of sufficient capacity to deliver at least 1000 ppm of the 2,6-dinitro-p-cresol or meta-nitro-para-cresol inhibitor into each distillation column. The capacity required for the pressurized vessel will depend upon the total volume of vinyl aromatic compound contained within each distillation column, and upon the concentration of the supplemental inhibitor solution. The specific capacity needed for the pressurized vessel will depend therefore upon the requirements of the particular distillation apparatus under consideration and can be readily ascertained by those skilled in the art once the volume of vinyl aromatic compound within each distillation column is determined.

The supplemental inhibitor solution may also be of any convenient concentration. Preferably, however, this solution comprises 25 wt. % 2,6-dinitro-p-cresol or meta-nitro-para cresol, as the case may be, in the aromatic hydrocarbon diluent, which preferably is ethylbenzene. At this concentration, the effective amount of inhibitor per ml of the diluent is maximized without exhibiting appreciable precipitation upon prolonged storage at room temperature.

In operation, a suitable quantity of the supplemental inhibitor solution is prepared, and then fed into the pressurized vessel. Periodically, it is also preferred to withdraw a small sample from the vessel in order to insure removal of any sediment and to protect against plugging of the vessel outlet upon prolonged disuse. In the event of an emergency situation in which the primary polymerization inhibitor addition system is rendered inoperative, or the primary polymerization inhibitor is inadequate to achieve sufficient polymerization control, the pressure within the vessel is then employed to force feed at least 1000 ppm of the supplemental inhibitor into each of the distillation columns of the distillation apparatus.

The method of the present invention is suitable for use in the separation of virtually any type of readily polymerizable vinyl aromatic compound from a mixture wherein the vinyl aromatic compound is subjected to a temperature above room temperature. In its most useful application, the method of the present invention is particularly useful for a distillation mixture containing one of the vinyl aromatic compounds selected from the group consisting of styrene, alpha-methylstyrene, vinyltoluene, vinylnapthalene, divinylbenzenes, alkylated styrene, and polyvinylbenzenes. The method of the present invention is particularly advantageous, however, for preventing the polymerization of a crude styrene mixture during distillation at elevated temperatures within a distillation apparatus which is subject to an emergency condition.

The emergency inhibitor system of the instant invention is also adaptable for use with any type of distillative separatory process wherein the readily polymerizable vinyl aromatic compound is subjected to temperatures above room temperature. For example, the emergency method of the instant conception is highly advantageous for use in atmospheric distillation techniques (i.e., open to the atmosphere), reduced pressure distillation techniques, and extractive distillation techniques.

Furthermore, the emergency inhibitor system of the instant invention may be used in conjunction with any distillation apparatus known to those skilled in the art. The present invention is equally advantageous for use with one column distillation apparatus or with distillation apparatus employing a plurality of columns. The instant invention may even be effectively utilized with flash evaporators. While the instant invention can be employed to inject a supplemental inhibitor at any location within a distillation column upon the occurrence of a contingency, the advantages of the instant invention are best obtained by injecting the supplemental inhibitor solution into the top portion of each distillation column. Injection at this point permits the widest distribution of the supplemental inhibitor, and thus optimizes polymerization control.

Referring to the drawing, the single figure illustrates the application of the present invention, for exemplary purposes, to a conventional styrene distillation train comprising a benzene-toluene fractionating column 2, referred to in the industry as a B-T column, a recycle or ethylbenzene column 3, and a finish column 4. It should be emphasized, however, that the present invention is applicable to any distillation apparatus and any distillative process for the separation of a vinyl aromatic compound well known to those skilled in the art. A heated crude styrene feed is introduced into the intermediate portion of the B-T column 2 through feedline 1. The B-T column 2 may be of any suitable design known to those skilled in the art and may contain any suitable number of vapor-liquid contacting devices, such as bubble cap trays, perforated trays, valve trays, etc. The column 2 is also equipped with a suitable reboiler 8 for supplying heat thereto.

During normal operation, a benzene and toluene overhead product is withdrawn from the B-T column 2 through line 6, and a ethylbenzene and styrene mixture is withdrawn through line 7 and circulated via pump 13 into the recycle column 3. The recycle column 3 may be also of any suitable design, including the single distillation path and double distillation path varieties. In the drawing, the recycle column 3 is illustrated as being of the double distillation path type. Reboiler means 15 and 16 are also provided for each path. Under distillation conditions, an ethylbenzene overhead product is recovered from the recycle column 3 through line 14, and a styrene bottoms is withdrawn through line 17 and transferred with the assistance of pump 18 into the finish column.

In the finish column 4, the styrene bottoms undergoes final treatment, yielding a high purity styrene overhead product through line 30, and a bottoms fraction which is subjected to further treatment in batch pot 5. The finish column 4 is also equipped with the boiler means 19 and a suitable pump 20 for circulating the bottoms therethrough.

During normal operating conditions, polymerization control is provided within the distillation apparatus by pumping a suitable inhibitor in a suitable hydrocarbon diluent, such as ethyl benzene, into the distillation train. In the drawing, the polymerization inhibitor feed lines are shown as comprising lines 9, 10, 11, and 12, line 10 supplying an effective quantity of the primary inhibitor to the B-T column, and lines 11 and 12 supplying the primary inhibitor to each of the distillation paths of the recycle column 3. Preferably, the primary polymerization inhibitor is fed into the top portion of the recycle column, since this addition system has been found to provide optimum distribution of the inhibitor within the recycle column and concomitantly more effective polymerization control.

The supplemental polymerization inhibitor system is shown as comprising pressurized vessel 23, and feed lines 24 through 28. As has been aforementioned, the pressurized vessel 23 may be of any suitable construction, but preferably is of the bottom dish feed type. The working capacity of this vessel is also sufficiently large to supply at least 1,000 ppm of the supplemental inhibitors to each of the distillation columns 2, 3, and 4. Suitably, the supplemental inhibitor is introduced into the top portion of each of the distillation columns in order to maximize inhibitor distribution, and thereby optimally inhibit polymerization of the vinyl aromatic compound.

Under normal operating conditions, the primary polymerization inhibitor system provides sufficient quantities of inhibitor to the distillation train to effectively control polymerization therein. However, in the advent of an emergency situation, such as a power outage, the primary inhibitor addition system is rendered inoperative. Moreover, the pumps 13 and 18 are also rendered inoperative. Consequently, a large volume of the styrene feed is trapped within the distillation train at an elevated temperature without any substantial heat transfer from the styrene feed contained in the respective distillation column bottoms. Heretofore, in the event of such a contingency, this large volume of styrene material depended upon the small quantity of inhibitor already present within the distillation train for polymerization control, a quantity inadequate to provide prolonged effective control of polymerization. Since many of the most effective polymerization inhibitors for distillation processes have relatively short half-lives, such limited quantities of inhibitor are inadequate to provide suitable polymerization control. With the utilization of the instant invention, however, upon happening of such an occurrence, suitable valve means 31 on the pressure vessel 23 is opened, releasing the supplemental inhibitor solution for introduction into each of the distillation columns 2, 3 and 4. By force feeding at least 1000 ppm of the 2,6-dinitro-p-cresol of the meta-nitro-para-cresol inhibitor solution into each of the distillation columns, the polymerization of the styrene mixture can be effectively controlled for prolonged periods while measures are taken to restore the distillation apparatus to normal operation.

Use of the emergency polymerization inhibitor system of the instant invention thus provides an effective means for controlling the polymerization of a vinyl aromatic compound within a distillation apparatus which is subject to an emergency condition. By providing an emergency system without an external energy requirement, effective polymerization control can be achieved within a distillation apparatus until corrective measures can be taken. Consequently, the present invention obviates a potentially dangerous situation, and prevents the possibility of damage to the distillation apparatus due to the formation of thermal polymer therein.

While the instant invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for preventing the polymerization of a readily polymerizable vinyl aromatic compound during distillation a distillation conditions of elevated temperature within a distillation apparatus having at least one distillation column, said vinyl aromatic compound containing a primary polymerization inhibitor system which is sufficient to substantially prevent polymerization of the vinyl aromatic compound under normal distillation conditions, said method comprising the steps of;

a. providing a pressurized solution of a polymerization inhibitor in an aromatic hydrocarbon diluent for use as a supplemental emergency polymerization inhibitor, said inhibitor being readily soluble in said diluent, said pressurized solution being selectively connected with each distillation column; and, b. force-feeding said solution into each distillation column of said distillation system in an amount sufficient to prevent polymerization of the vinyl aromatic compound therein in response to a change in distillation conditions which renders said primary polymerization inhibitor inoperative for its intended purpose.

2. The method of claim 1, wherein said supplemental polymerization inhibitor is selected from the group consisting of 2,6-dinitro-p-cresol and meta-nitro-para-cresol.

3. The method of claim 2 wherein said supplemental inhibitor is 2,6-dinitro-p-cresol.

4. The method of claim 2 wherein said supplemental inhibitor is meta-nitro-para-cresol.

5. The method of claim 2, wherein said vinyl aromatic compound is selected from the group consisting of styrene, substituted, styrene, vinyl toluene, vinyl naphthalene, divinyl benzenes, and polyvinyl benzenes.

6. The method of claim 5, wherein said vinyl aromatic compound is styrene.

7. The method of claim 2, wherein at least 1000 ppm of said supplemental polymerization inhibitor are force fed into each of the distillation vessels.

8. The method of claim 1, wherein said aromatic hydrocarbon diluent is selected from the group consisting of benzene, toluene, ethyl benzene, and styrene.

9. The method of claim 8, wherein said diluent is ethyl benzene.

10. The method of claim 2, wherein said supplemental polymerization inhibitor is injected into the top portion of each of the said distillation vessels.

11. The method of claim 2, wherein said pressurized solution of said supplemental polymerization inhibitor in said aromatic hydrocarbon diluent comprises 25% by weight of said supplemental polymerization inhibitor.